United States Patent
Meredith et al.

(10) Patent No.: US 10,799,704 B2
(45) Date of Patent: Oct. 13, 2020

(54) PROXIMITY-BASED SECURITY FOR IMPLANTED MEDICAL DEVICES

(71) Applicant: AT&T Intellectual Property I, L.P., Atlanta, GA (US)

(72) Inventors: Sheldon Meredith, Roswell, GA (US); Peter Hardie, Cumming, GA (US); William C. Cottrill, Canton, GA (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 183 days.

(21) Appl. No.: 15/982,484

(22) Filed: May 17, 2018

(65) Prior Publication Data

US 2019/0351243 A1   Nov. 21, 2019

(51) Int. Cl.
*A61N 1/372* (2006.01)
*G06F 8/65* (2018.01)
*G06F 8/61* (2018.01)

(52) U.S. Cl.
CPC ..... *A61N 1/37217* (2013.01); *A61N 1/37264* (2013.01); *G06F 8/65* (2013.01);
(Continued)

(58) Field of Classification Search
CPC ............ A61N 1/37217; A61N 1/37254; A61N 1/37264
See application file for complete search history.

(56) References Cited

U.S. PATENT DOCUMENTS 5,725,559 A   3/1998   Alt et al.
6,889,086 B2  5/2005   Mass et al.
(Continued)

FOREIGN PATENT DOCUMENTS

WO   2008021920   2/2008
WO   2017027729   2/2017

OTHER PUBLICATIONS

D. Halperin, T. S.Heydt-Benjamin, B. Ransford, S. S. Clark, B. Defend, W. Morgan, . . . , "Pacemakers and implantable cardiac defibrillators:Software radio attacks and zero-power defenses," in Proc. IEEE Symp. Security & Privacy, 2008, pp. 129-142 (Year: 2008).*

(Continued)

*Primary Examiner* — William J Levicky
(74) *Attorney, Agent, or Firm* — Kilpatrick Townsend & Stockton LLP

(57) ABSTRACT

A proximity-based security mechanism can control access to the programming interface of an implanted medical device. The security mechanism prevents unauthorized remote access to the programming interface by hackers or other hostile individuals, securing the safety of the subject. The system also allows the subject or other responsible person to activate the programming interface when changes to the operation of the implanted medical device are needed. In one example, a security interface is operable to detect, while implanted in the subject, an activation signal produced in close proximity to the subject, and activate the programming interface in response to the activation signal so that the implantable medical device can receive the programming instructions. A proximity-based security mechanism can be a dedicated device, or can be implemented in a programmable computing device such as a smartphone or other mobile computing device.

18 Claims, 6 Drawing Sheets

(52) U.S. Cl.
CPC ...... *A61N 1/37254* (2017.08); *A61N 1/37276* (2013.01); *G06F 8/64* (2013.01)

(56) References Cited

U.S. PATENT DOCUMENTS

| | | | |
|---|---|---|---|
| 7,406,349 | B2 | 7/2008 | Seeberger et al. |
| 7,890,180 | B2 | 2/2011 | Quiles |
| 8,015,024 | B2 | 9/2011 | Disilvestro et al. |
| 8,290,515 | B2 | 10/2012 | Staton et al. |
| 8,321,913 | B2 | 11/2012 | Turnbull et al. |
| 8,995,949 | B2 | 3/2015 | Roberts et al. |
| 9,445,264 | B2 | 9/2016 | Young et al. |
| 9,479,267 | B1 | 10/2016 | Bolin et al. |
| 9,687,658 | B2 | 6/2017 | Wu et al. |
| 9,747,431 | B2 | 8/2017 | Chow |
| 9,769,141 | B2 | 9/2017 | Brannon |
| 9,838,082 | B2 | 12/2017 | Dobyns et al. |
| 9,855,433 | B2 | 1/2018 | Shahandeh et al. |
| 2005/0065815 | A1 | 3/2005 | Mazar et al. |
| 2009/0125084 | A1* | 5/2009 | Juels .................... A61B 5/0031 607/60 |
| 2009/0270949 | A1 | 10/2009 | Kalpin et al. |
| 2010/0085160 | A1 | 4/2010 | Fu |
| 2010/0300159 | A1* | 12/2010 | Berg ..................... C09J 9/02 70/58 |
| 2011/0219427 | A1 | 9/2011 | Hito et al. |
| 2013/0176106 | A1 | 7/2013 | Schultz et al. |
| 2015/0089590 | A1 | 3/2015 | Krishnan et al. |
| 2017/0140644 | A1 | 5/2017 | Hwang et al. |
| 2017/0161449 | A1 | 6/2017 | Meskens |
| 2017/0372600 | A1 | 12/2017 | Palin et al. |
| 2018/0028827 | A1 | 2/2018 | Schilling et al. |
| 2018/0043168 | A1* | 2/2018 | Kim .................... A61N 1/37217 |
| 2018/0109946 | A1* | 4/2018 | Mosenia .............. A61N 1/3727 |

OTHER PUBLICATIONS

Camara et al., Security and Privacy Issues in Implantable Medical Devices: A Comprehensive Survey, Journal of Biomedical Informatics, vol. 55, Jun. 2015, pp. 272-289.

* cited by examiner

PROXIMITY-BASED SECURITY FOR IMPLANTED MEDICAL DEVICES

TECHNICAL FIELD

This disclosure generally relates to providing programming-interface security for implanted medical devices. More specifically, this disclosure relates to security mechanisms that operate at least partly based on physical proximity.

BACKGROUND

As increasing numbers of people receive implanted medical devices, the threat of hackers or others intentionally or accidently connecting to those devices wirelessly also increases. Access security for the programming interfaces for these medical devices can be challenging. Generally, the devices use an indirect programming interface to avoid insulting protective skin. The indirect interface may be subject to attacks and unauthorized reprogramming. The risk may be increased for high-profile individuals such as political figures and wealthy individuals. Regretfully, bad actors may hurt others simply because they can or for some other agenda. A medical device may also be susceptible to accidental reprogramming, for example, in environments where multiple individuals with implanted medical devices may be present. Preventing unauthorized access to programmable medical devices, while allowing access quickly and efficiently for emergency personnel to adjust device parameters if needed is challenging.

SUMMARY

In one example, a system includes an implantable medical device including a programming interface to receive programming instructions in vivo in a subject to control operations of the implantable medical device, and a security interface coupled to the implantable medical device in vivo to prevent access to the programming interface except in response to receiving a coded activation signal produced ex vivo in proximity to the subject to allow the programming interface to receive the programming instructions.

In another example, a method includes detecting, at or near a medical device implanted in a subject, a coded activation signal produced in close proximity to the subject, activating a programming interface for the medical device in response to the coded activation signal, and receiving programming instructions over the programming interface while the programming interface is activated.

In another example, a non-transitory computer-readable medium includes instructions that are executable by a computing device for causing the computing device to perform operations for activating a programming interface of a medical device implanted in a subject. The operations include receiving input from a user directed to authenticating access to the programming interface of the medical device, and transmitting an authentication signal comprising at least one of an acoustic signal or an optical signal configured to activate the programing interface when the computing device is in close proximity to the subject.

BRIEF DESCRIPTION OF THE FIGURES

These and other features, aspects, and advantages of the present disclosure are better understood when the following Detailed Description is read with reference to the accompanying drawings.

DETAILED DESCRIPTION

Figure 1:
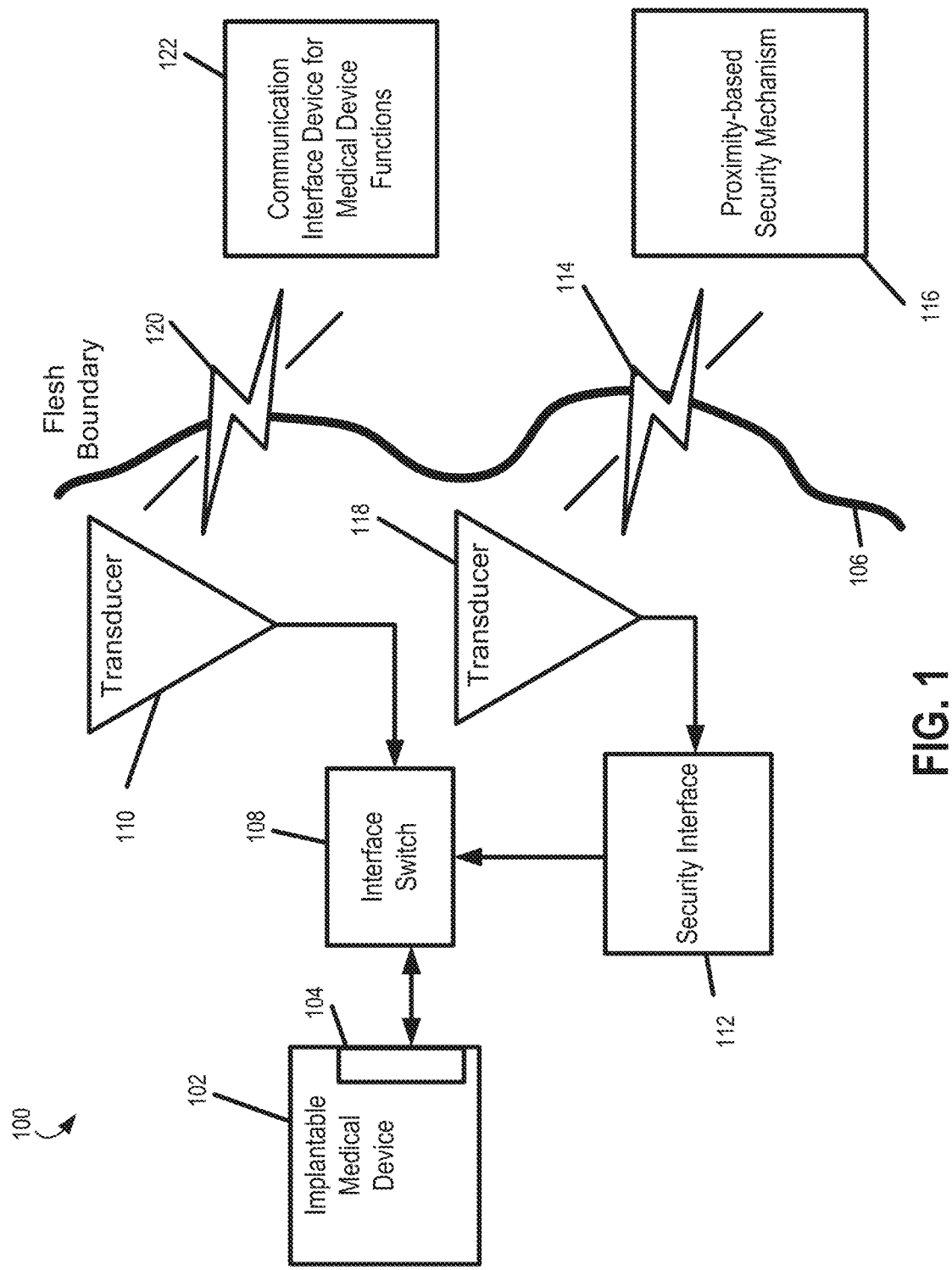
FIG. 1 is a block diagram depicting a system for proximity-based security for an implantable medical device according to some aspects.

Certain aspects of this disclosure relate to controlling the access to the programming interface of an implantable medical device. Unauthorized remote access to the programming interface by hackers or other individuals can be prevented. Certain aspects can also allow the subject or an approved person to activate the programming interface to program the implanted medical device.

In one example, a controlled security mechanism can control access to the programming interface receiver of the implantable medical device. The controlled security mechanism can prevent access to the implanted device by devices other than those in proximity to the subject. If the controlled security mechanism is present, the receiver of the medical device can be activated, and reprogramming or reconfiguration can be performed. To provide additional security against inadvertent environmental activation, in certain aspects, a coded activation signal that is unlikely to be naturally occurring can be used. The term "subject" as used herein is intended to represent not only a human patient into which a medical device has been planted, but also an animal as implantable medical devices can be used in veterinary practice or animal management. The term "user" is intended to refer to anyone who is legitimately interacting with or enabling an interface of an implanted medical device, including, but not limited to, a patient, medical care provider, or first responder.

As an example, a security mechanism can be a battery-operated hand-held device that can be placed near a patient with an implanted medical device. Programming instructions, commands, changes to settings, etc. cannot be provided to the implanted medical device unless the hand-held device is present close to the patient. By designing the hand-held device to require immediate proximity to the implanted medical device, and therefore to the patient in order to enable programming access to the implanted medical device, unauthorized remote reprogramming of the implanted medical device is prevented. As a more detailed example, the implanted medical device can include a magnetic switch that closes in the presence of a moderately strong, coded magnetic field applied to the skin directly over the magnetic switch. The magnetic field is generated by the battery-operated, hand-held device. Because magnetic fields decrease with the square of distance, the odds of nefarious activation from more than a few feet away from the patient are small, even if an unauthorized individual were to come into possession of the appropriate hand-held device. In another more detailed example, an optically triggered switch is used in the implanted medical device. By using a battery-operated, hand-held security device that generates wavelengths of light that are transmitted easily through skin, the optically triggered switch can be activated for a period of time sufficient for the authorized person with the hand-held device to provide programming or setting updates to the implanted medical device. A coding scheme can prevent inadvertent switch activation from random light sources. An acoustically triggered switch can also be used in the implanted medical device, with the battery-operated, hand-held device generating sound patterns.

The hand-held security device, as an example, can be a special-purpose device with an appropriate signaling transducer and a processing device in the form of a microcontroller or digital signal processor. The hand-held security device, as another example, can be a general-purpose computing device such as a smartphone, personal computer, or tablet computer. In such a case, the proximity-based security mechanism is implemented by an application (an "app"), which can be installed on the general-purpose computing device.

Detailed descriptions of certain examples are discussed below. These illustrative examples are given to introduce the reader to the general subject matter discussed here and are not intended to limit the scope of the disclosed concepts. The following sections describe various additional aspects and examples with reference to the drawings in which like numerals indicate like elements, and directional descriptions are used to describe the illustrative examples but, like the illustrative examples, should not be used to limit the present disclosure.

FIG. 1 depicts an example of a system 100 for providing proximity-based security for an implantable medical device 102 according to some aspects. The implantable medical device 102 can receive programming instructions through programming interface 104. Implantable medical device 102 can be implanted in a subject having flesh boundary 106 such that the left-hand side of the flesh boundary 106 is in vivo to the subject and the right-hand side of the flesh boundary 106 is ex vivo to the subject. System 100 also includes an interface switch 108 to control access to implantable medical device 102 by enabling and disabling programming interface 104. In some aspects, interface switch 108 enables or disables programming interface 104 by interrupting the programming interface's connection to a first transducer 110. A security interface 112 can be communicatively coupled to implantable medical device 102 through the interface switch 108. Security interface 112 can detect activation signal 114 that can be received through flesh boundary 106 from a proximity-based security mechanism 116 that can generate an activation signal in close proximity to the subject. Security interface 112 can receive activation signal 114 using second transducer 118. If the appropriate activation signal is received, security interface 112 can close interface switch 108 to allow programming instructions to be received by the programming interface 104. In some aspects, the instructions are carried by signal 120 that is communicated by communication interface device 122. Communication interface device 122 can provide programming instructions for medical device functions carried by signal 120. Signal 120 is received using transducer 110. As used herein, the phrase "programming instructions" can include, but is not limited to, program code in the traditional sense, such as may be transmitted to the implantable medical device to provide a software or firmware update. The term "programming instructions" can also include or refer to one or more operational setting values for the implantable medical device that are input by a user such as a physician using communication interface device 122.

In some aspects, activation signal 114 of FIG. 1 is a magnetic field sensed by transducer 118 so that interface switch 108 acts as a magnetic switch for implantable medical device 102. The magnetic switch can close in the presence of a moderately strong magnetic field applied to the skin directly over transducer 118. In such a case, proximity-based security mechanism 116 produces the magnetic field. Because magnetic fields decrease in intensity with the square of distance, the odds of nefarious activation from more than a few feet from the subject are small. Further, if the subject were to inadvertently be in the presence of a strong magnetic field, the magnetic field wouldn't necessarily harm the programming mechanism, but would simply open the switch to allow programming to occur. Additional security can be obtained by using a coded magnetic field instead of a static magnetic field. Such coding can be imparted, as an example, by applying pulsing in a predetermined pattern to create a pulsed magnetic field. The magnetic field can include a predetermined pattern or a pulse frequency that is specifically assigned to the implantable medical device.

In another aspect, interface switch 108 of FIG. 1 acts as an optically triggered switch, where activation signal 114 is an optical signal. By using wavelengths of light that are transmitted easily through skin and an on-off coding scheme, interface switch 108 can be activated for a period of time sufficient to perform the configuration or software download. The coding scheme prevents inadvertent switch activation from random light sources. A measure of light intensity can also be used to ensure activation only occurs if the proximity-based security mechanism, which includes the light source, is essentially in direct contact with the skin. For even greater security, the coding scheme can be specific to the specific implantable medical device and thus to the subject, meaning any user trying to use coded light to activate interface switch 108 would need to know a secure code.

In another aspect, interface switch 108 of FIG. 1 acts as an acoustically operated switch where activation signal 114 is an acoustic signal and a coded tone or set of tones is presented by an ultrasound or audible generator that is included in proximity-based security mechanism 116. Again, frequency and pulse coding can eliminate random activation from background audio and the coding scheme can be specific to the specific implantable medical device and thus to the subject, meaning any user trying to use audio tones to activate interface switch 108 would need to know a secure code. The code can be applied based on carrier frequency or pulse frequency in the case of pulse modulation, either a frequency or a set of frequencies being specifically assigned to an implantable medical device.

In the system of FIG. 1, interface switch 108 and security interface 112 in some aspects can each be implemented in hardware, software, firmware, or some combination of the foregoing. The functions of some or all of the implantable medical device 102, interface switch 108, and security interface 112, and of one or both transducers 110 and 118, can be combined into a single physical device. But, in some aspects, at least the function of the security interface 112 and the programming interface 104 are isolated so that the proximity-based security mechanism 116 enables two-factor authentication within system 100. Proximity-based security mechanism 116 serves as the "second" authentication factor because security credentials are also required to initiate the reception of instructions through programming interface 104 from communication interface device 122. The security credentials can include an authentication key or password known only to the implantable medical device, an authorized medical system, and authorized users.

System 100 of FIG. 1 is illustrated schematically, meaning that the various components can be arranged in various ways and the communication interface device 122 may be further from the subject than proximity-based security mechanism 116. In some aspects, communication interface device 122 enables remote programming from a server connected through a cloud network or the Internet. In such a case, only the proximity-based security mechanism 116 is necessarily in close proximity to the subject with implantable medical device 102. The phrase "close proximity" is intended to describe distances within those expected in a typically sized room that might be used for medical treatment. Such distances, as an example, might be anywhere from essentially zero meters, when the proximity-based security mechanism is in contact or near contact with the skin, to several meters. As further examples, the proximity-based security mechanism may operate within one meter or within two meters of the subject. In order to maintain acceptable security, the proximity-based security mechanism should not be able to trigger the interface switch from greater distances, since this capability would allow a nefarious individual to trigger the interface switch from a position outside the view of the subject or user.

Figure 2:
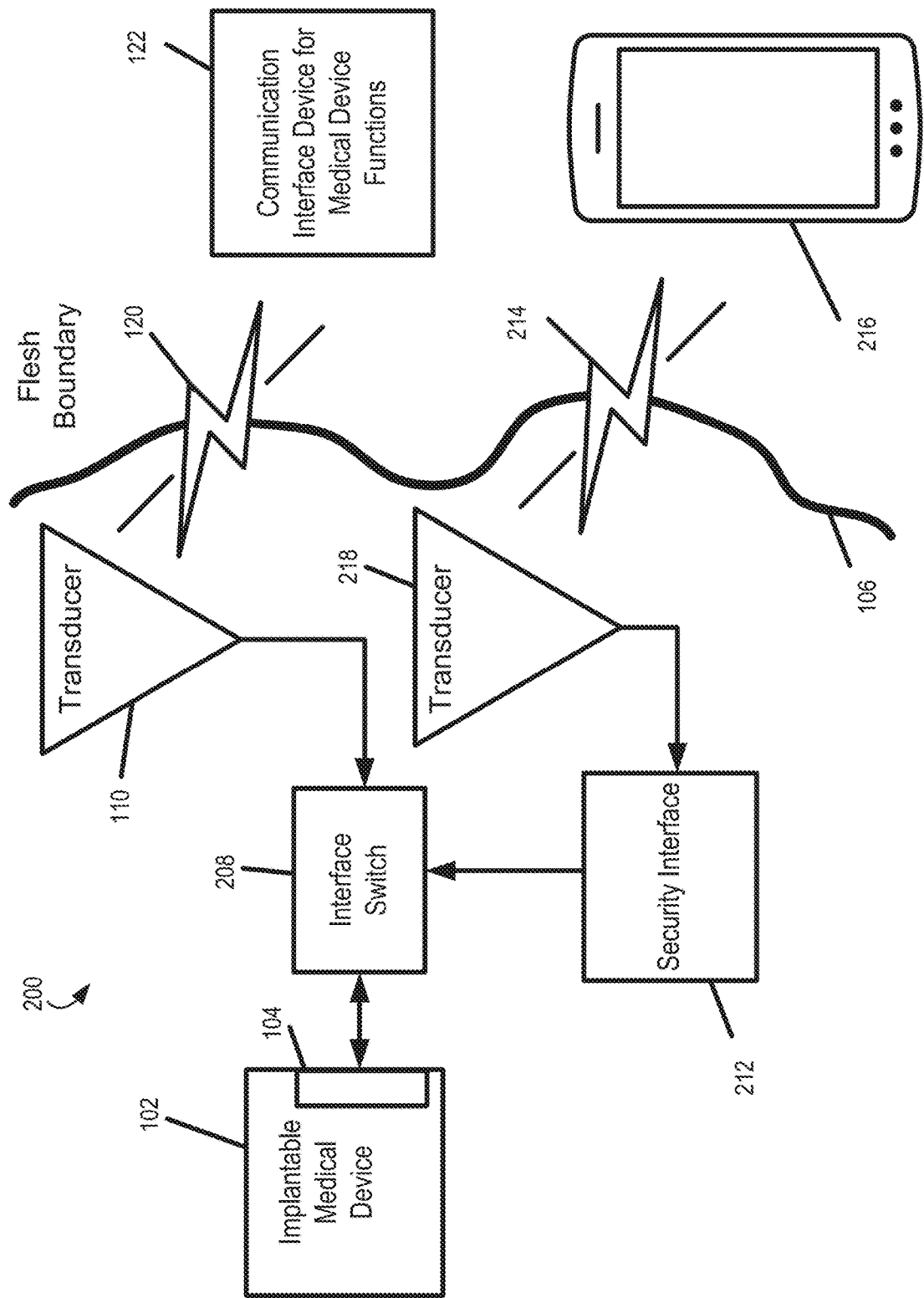
FIG. 2 is a block diagram depicting a system for proximity-based security for an implantable medical device according to additional aspects.

A proximity-based security mechanism according to some aspects is a dedicated hardware-based device, a dedicated software-based device, a dedicated firmware-based device, or a combination of these. For example, a dedicated software-based device may be a device with an appropriate signaling transducer and a processing device in the form of a microcontroller or digital signal processor. In such a case on-board memory, either separate from or built-in to the processing device includes non-transitory computer program code instructions to cause the processing device to interact with the security interface in or on the subject. The proximity-based security mechanism according to other aspects may be implemented in a general-purpose computing device such as a smartphone, personal computer, or tablet computer. In such a case, the proximity-based security mechanism is implemented by an application (an "app"), which can be installed on the general-purpose computing device. FIG. 2 illustrates a system in which a general-purpose computing device is used to implement the proximity-based security mechanism according to some aspects.

System 200 of FIG. 2 implements proximity-based security for an implantable medical device according to some aspects. System 200 includes some of the same or similar components illustrated as part of system 100 as indicated by the use of like reference numbers, however, some other components are configured for use with a general-purpose computing device as the proximity-based security mechanism. System 200 includes implantable medical device 102 that receives programming instructions through programming interface 104. Implantable medical device 102 is implanted in a subject having flesh boundary 106. System 100 also includes an interface switch 208. Interface switch 208 controls access to implantable medical device 102 by enabling and disabling programming interface 104. In some aspects, interface switch 208 enables or disables programming interface 104 by interrupting the programming interface's connection to a first transducer 110 as before. A security interface 212 is communicatively coupled to implantable medical device 102 through the interface switch 208.

In the example of system 200 of FIG. 2, security interface 212 is operable to detect activation signal 214 received through flesh boundary 106 from a proximity-based security mechanism implemented by a mobile computing device 216, a smartphone that will be discussed in more detail below with respect to FIG. 4. Security interface 212 receives activation signal 214 using second transducer 218. Activation signal 214 can be an acoustic signal or optical signal as previously discussed, in either case generated by the smartphone hardware under control of an appropriate app. A combination of acoustic and optical signals can also be used. If the appropriate activation signal is received, security interface 212 closes interface switch 108 to allow programming instructions to reach programming interface 104. In this example, these instructions are again carried by signal 120 that is communicated by communication interface device 122, which provides programming instructions for medical device functions. The instructions can be carried by signal 120 as received using transducer 110.

Figure 3:
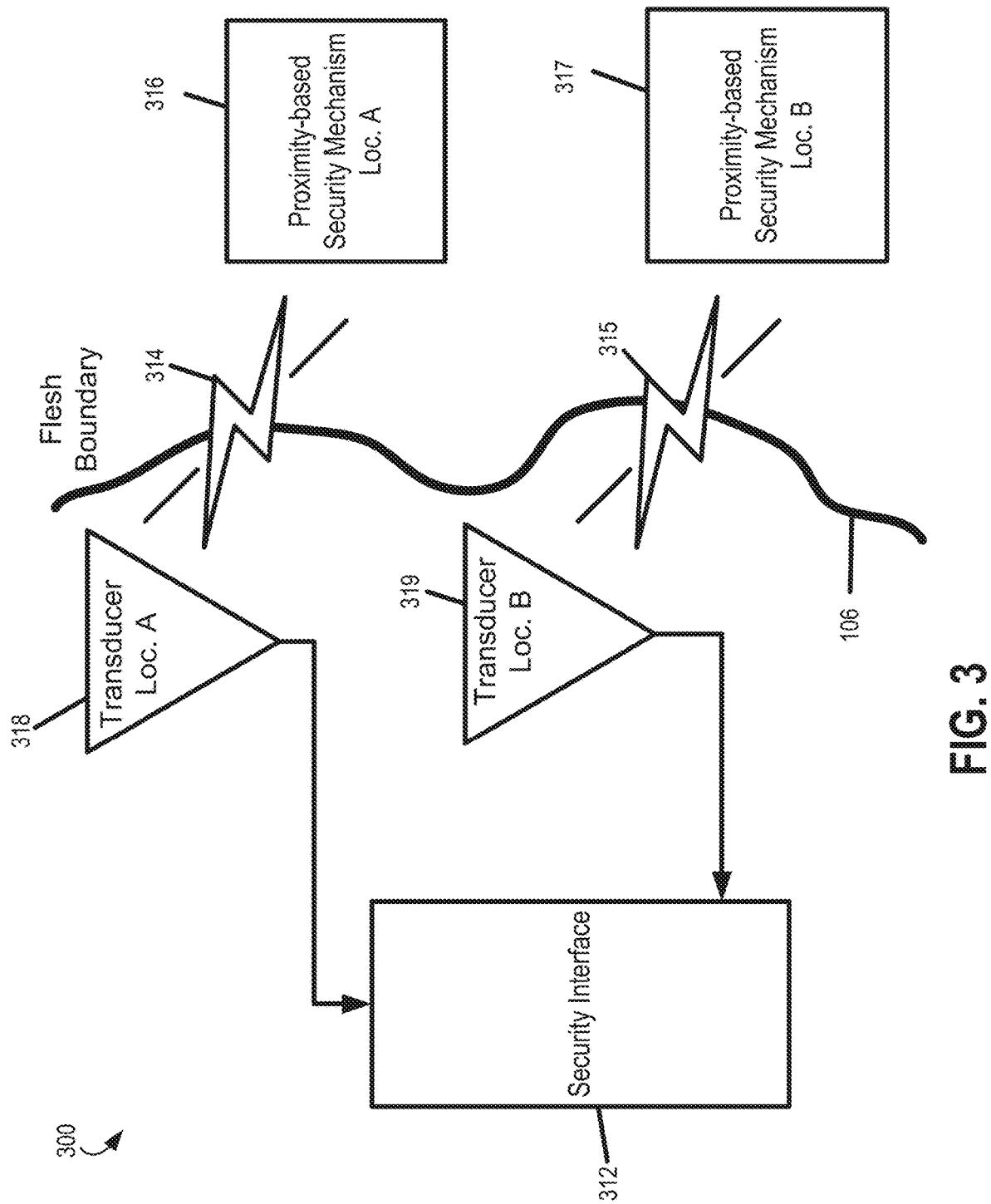
FIG. 3 is a block diagram depicting a system for proximity-based security for an implantable medical device according to further aspects.

FIG. 3 illustrates a portion of system 300, namely, the security interface and signaling components. It should be understood that the implantable medical device and other previously discussed components may be included in such a system, but have been omitted from FIG. 3 for clarity of illustration. System 300 includes a security interface 312 that is configured to receive two or more signals from two or more proximity-based security mechanisms. Activation signal 314 is transmitted by proximity-based security mechanism 316 to first location transducer 318. Activation signal 315 is transmitted from proximity-based security mechanism 317 to second location transducer 319. In some aspects, two different signal types can be used. For example, both a magnetic signal and an optical signal could be used to enhance the security of the system. The two proximity-based security mechanisms can be implemented in a unitary device. Alternatively, as in system 300 illustrated in FIG. 3, two signals of the same or different type are applied in proximity to two different places on the body of the subject or near different parts of flesh boundary 106, such as location A and location B. Thus, instead of a single activation signal, two or more spatially diverse activation signals are used.

The signals described above with respect to system 300 of FIG. 3 may any signal types and be coded in any of the ways previously discussed for a given signal type. For example, both magnetic signal and an optical signal can be required for activation of the interface switch. Other forms the two activation signals can take include multiple frequencies of light or sound, or a time-based variation, such as two different predetermined patterns for a flashing light, a pulsing magnetic field, or both. The system could also require that different conditions are sensed at the same time, such as one transducer sensing light, the other no light, or both receiving a time-coded signal, but not synchronized. In such implementations, an attempt to activate the programming interface for the implanted medical device from a distance would fail because the signaling could not meet the required activation conditions. A user can use a mobile computing device app to generate simultaneous light pulses and tone sequences. Since the system still requires close proximity with these bi-modal signaling implementations, the signaling specifics don't necessarily need to be kept completely secret, but could be provided to and kept on-hand by first responders and medical personnel.

Figure 4:
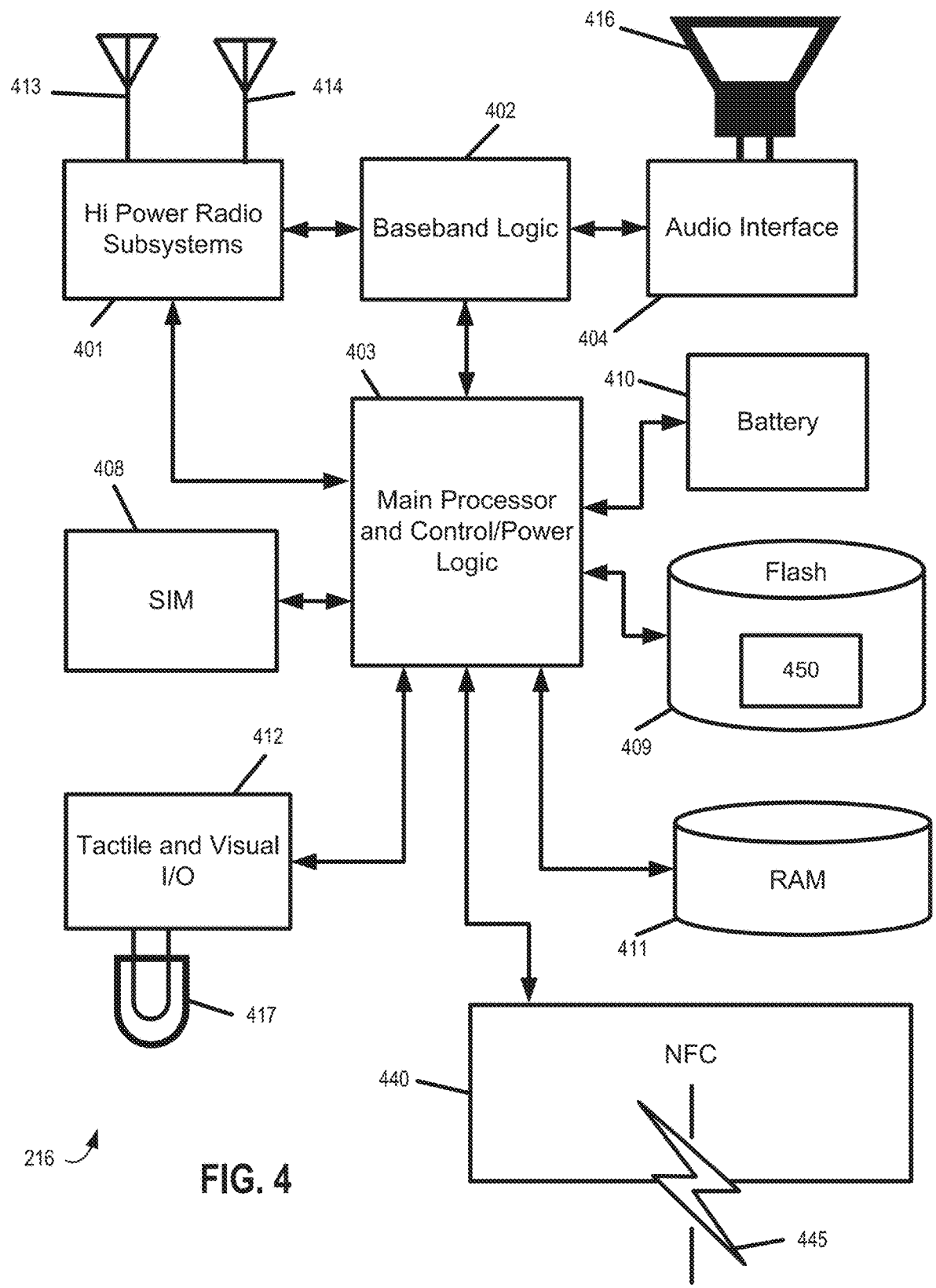
FIG. 4 is a block diagram depicting a computing device for implementing a proximity-based security mechanism for an implantable medical device according to some aspects.

FIG. 4 is a block diagram depicting a computing device for implementing a proximity-based security mechanism for an implantable medical device according to some aspects. Referring now to FIG. 4, the exemplary mobile computing device 216 from FIG. 2 will be described detail. The mobile device of FIG. 4 includes a high power (hi power) radio subsystems block 401, a baseband logic block 402, a main processor and control logic block ("main logic") 403, and an audio interface block 404. A subscriber identity module (SIM) 408 is shown as operatively connected to the main processor and control logic. Also included is flash memory 409, a battery 410, and random access memory (RAM) 411. The RAM 411 may in some aspects include various devices and possibly memory dedicated to specific purposes such as graphics. A portion of RAM 411 may be used to store the data currently being viewed on the display of the mobile device. The display (not shown) is part of tactile and visual input/output (I/0) block 412. Within the high power radio subsystems block 401, the transmit and receive information is converted to and from the radio frequencies (RF) of the various carrier types, and filtering using baseband or intermediate frequency circuitry is applied. Radio subsystems for more local communication such as for Wi-Fi are included in this block. The device's main antenna system 413 is communicatively coupled to the radio subsystems block 401. The device also includes a Wi-Fi antenna 414. In the baseband logic block 402, basic signal processing occurs, e.g., synchronization, channel coding, decoding and burst formatting.

Still referring to FIG. 4, the audio interface block 404 handles voice as well as analog-to-digital (A/D) and D/A processing. It also produces output through speaker 416. The output may include acoustic signaling to implement the proximity-based security mechanism using audible or ultrasonic tones as previously discussed. Similarly, the tactile and visual input/output (I/0) block 412 can produce output through lamp 417 such as light flashes to implement the proximity-based security mechanism using optical signaling as previously discussed. The main logic 403 coordinates the aforementioned blocks and also plays an important role in controlling the interface components such as a screen and touch interface or keyboard. The functions of the aforementioned blocks are directed and controlled by a processing device or processing devices included in the main logic, such as general-purpose microprocessors, digital signal processors (DSPs), application specific integrated circuits (ASICs), various types of signal conditioning circuitry, including analog-to-digital converters, digital-to-analog converters, input/output buffers, etc. The mobile device, in some aspects, communicates with external devices via a bi-directional, short-range near-field communication (NFC) interface 440. In addition to the previous examples, the activation signal directed to the security interface of the implantable device can be an electromagnetic signal 445 following NFC protocol, since NFC operates only when devices are in close proximity. A frequency of about 13.56 MHz is used for at least some standard, near field communication. However, other frequencies can be used as long as the frequency is known.

The flash memory 409 shown in FIG. 4 includes at least one array of non-volatile memory cells. RAM 411 includes at least one array of dynamic random access memory (DRAM) cells. The content of the flash memory may be pre-programmed and write protected thereafter, whereas the content of other portions of the RAM may be selectively modified and/or erased. The flash memory therefore, is non-transitory computer-readable medium that is used to store operating system software and application programs (apps), including an app 450, which includes instructions executable by computing device 216 to carry out the proximity-based security mechanism function described herein. RAM may be used to store, temporarily, code or frequency values to be applied to an activation signal, credentials or other data. The computing device of FIG. 4 may also be used to send programming instructions (commands or updates) to an implantable medical device. In some examples, these would be relayed or generated through an Internet server and ultimately transmitted to the implantable medical device through the communication interface device 122 for medical device functions.

Any computing device that is used as or implements a proximity-based security mechanism as described herein may contain many of the same elements discussed above with respect to FIG. 4. As an example, a dedicated device includes a main processor device, control, and power logic, RAM, flash memory, a battery, and the audio and visual I/O. The processing device can execute one or more operations for transmitting, receiving, and decoding signals. The processing device can execute instructions stored in a non-transitory memory device to perform the operations. The processing device can include one processing device or multiple processing devices. Non-limiting examples of a processing device include a field-programmable gate array ("FPGA"), an application-specific integrated circuit ("ASIC"), a microprocessing device, etc.

A memory device storing computer program instructions executable by the processing device can include any type of memory device that retains stored information when powered off. A computer-readable medium can include electronic, optical, magnetic, or other storage devices capable of providing the processing device with computer-readable instructions or other program code. Such a medium may store the instructions on a server prior to installation in or programming of a proximity-based security mechanism. Non-limiting examples of a computer-readable medium include (but are not limited to) magnetic disk(s), memory chip(s), read-only memory (ROM), random-access memory ("RAM"), an ASIC, a configured processing device, optical storage, or any other medium from which a computer processing device can read instructions.

Figure 5:
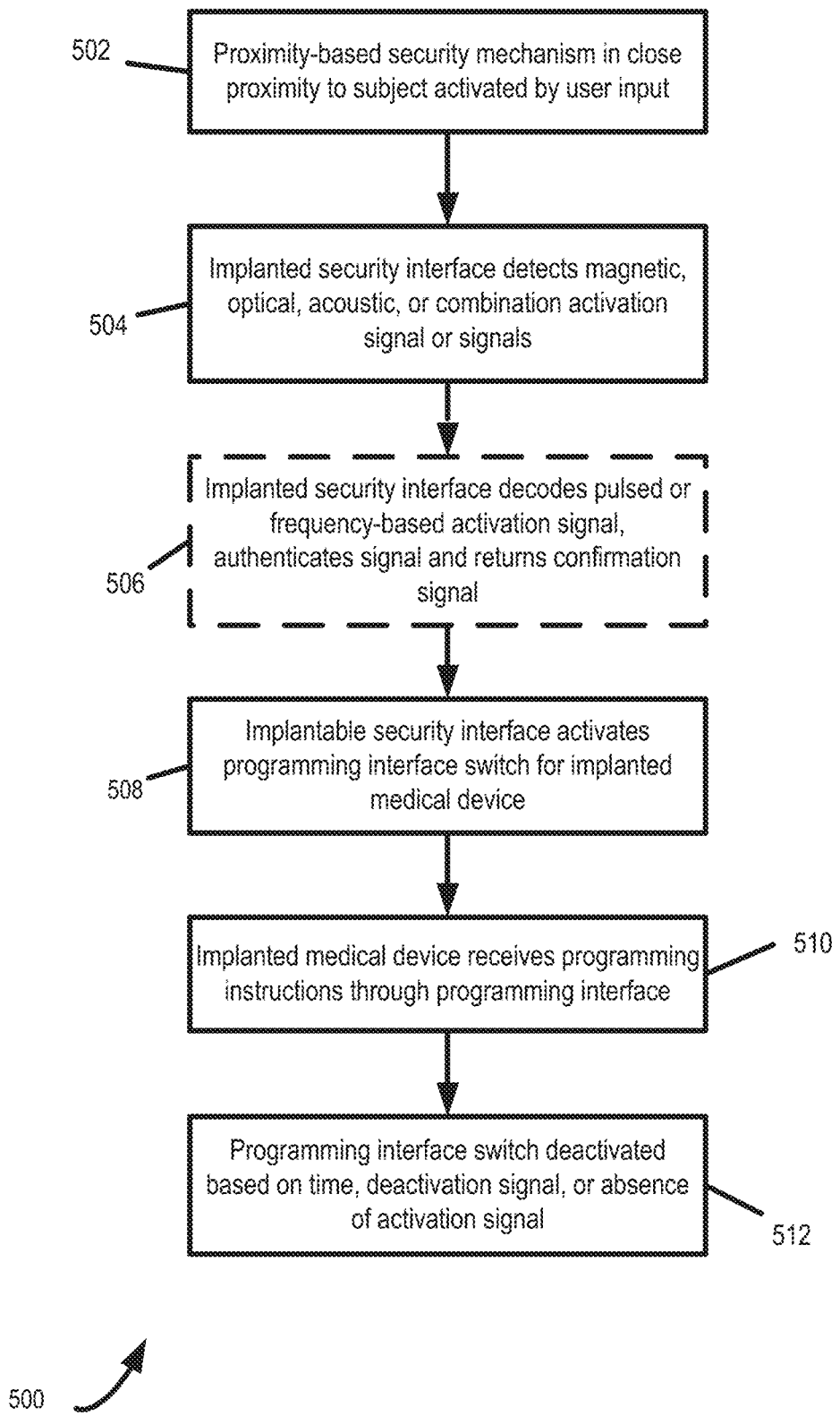
FIG. 5 is a flowchart illustrating a process for providing proximity-based security for an implantable medical device according to some aspects.

FIG. 5 depicts a flowchart illustrating a process for providing proximity-based security for an implantable medical device according to some aspects. Process 500 of FIG. 5 will be described with reference to the system diagram of FIG. 1. At block 502, proximity-based security mechanism 116 in close proximity to the subject receives input from a user indicating that the user wishes to activate the programming interface for implantable medical device 102. At block 504, implanted security interface 112 detects the activation signal or signals from the proximity-based security mechanism at or near the implantable medical device. At block 506, if the activation signal is coded, implanted security interface 112 decodes the activation signal, authenticates the signal, and optionally returns a confirmation signal. This confirmation signal, if used, would typically be received back through the network via the communication interface device 122. At block 508, implanted security interface 112 activates programming interface switch 108 for implantable medical device 102 in response to the activation signal. At block 510, implantable medical device 102 receives programming instructions through programming interface 104. When programming is complete, programming interface switch 108 is deactivated, for example, based on time, a deactivation signal, or the continued absence of an activation signal at block 512.

Figure 6:
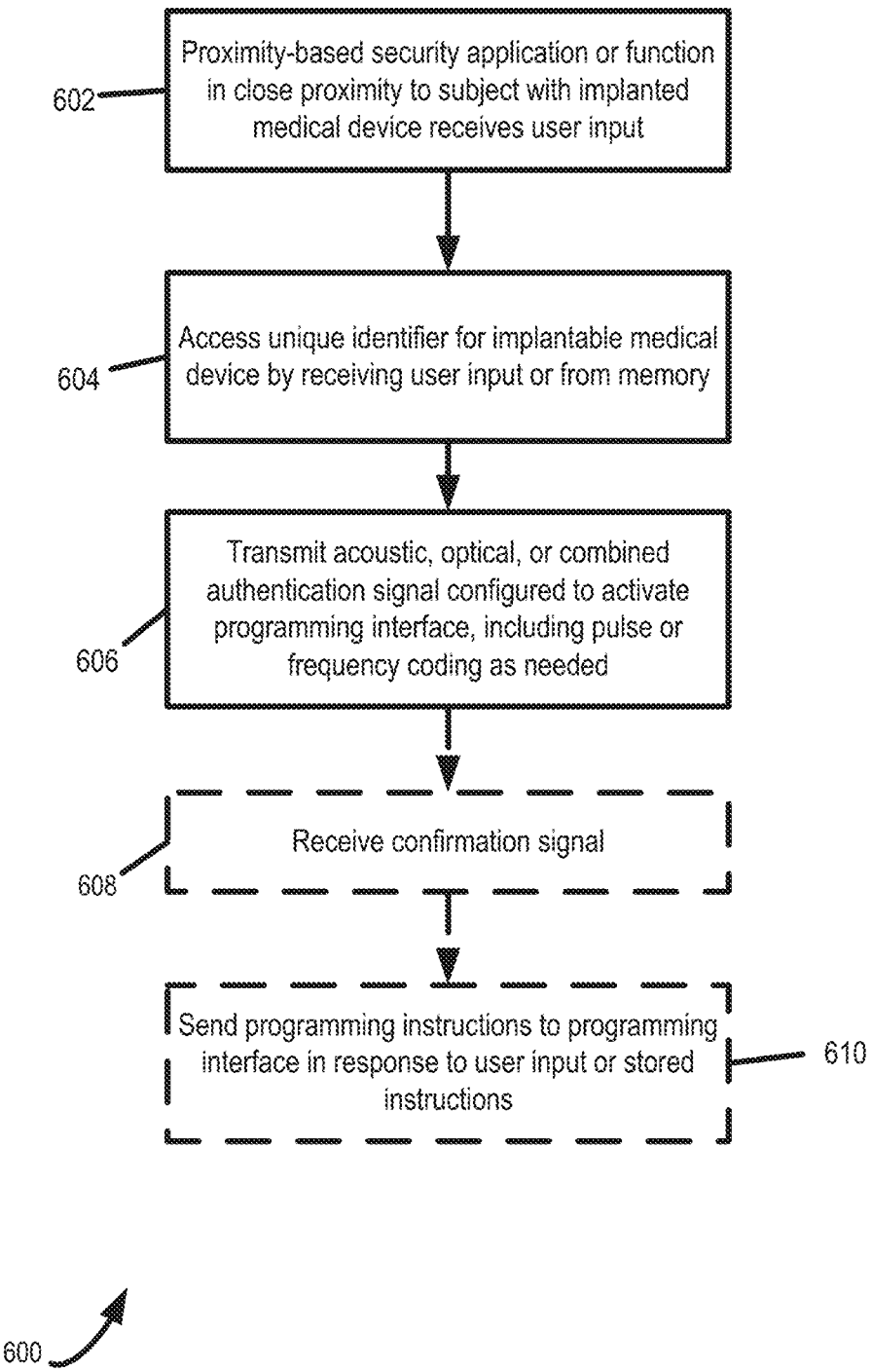
FIG. 6 is a flowchart showing the operation of a computing device implementing a proximity-based security mechanism for an implantable medical device according to some aspects.

FIG. 6 depicts a flowchart showing the operation of a computing device implementing a proximity-based security mechanism for an implantable medical device according to some aspects. Process 600 will be described with respect to the computing device of FIG. 4. At block 602, main logic 403 receives user input indicating a desire to activate the proximity-based security application or function in the device in order to authenticating access to the programming interface of the implantable medical device while in close proximity to the subject. Main logic 403 receives the input through tactile and visual I/0 412. At block 604, main logic 403 accesses a unique identifier for the implantable medical device. This identifier may be accessed by receiving additional user input, or maybe retrieved from flash memory 409. The identifier is used to code the authentication signal for the implantable medical device. At block 606, computing device 216 transmits acoustic, optical, or combine authentication signal configured to activate the programming interface in the implantable medical device. This activation signal includes pulse frequency coding as needed. At block 608, a confirmation signal is optionally received by computing device 216. This confirmation signal would typically be received back through the network via the communication interface device 122 and the Wi-Fi or cellular interface of computing device 216, though a system could be designed to send confirmation signals back through the NFC interface 440. At block 610, programming instructions are optionally sent through the programming interface of the implantable medical device. The programming instructions may be received through user input and temporarily stored in RAM 411, may be retrieved from a server, or may be retrieved from flash memory 409.

Unless specifically stated otherwise, throughout this specification terms such as "processing," "computing," or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computing systems accessing stored software that programs or configures the computing system from a general-purpose computing apparatus to a specialized computing apparatus implementing one or more aspects of the present subject matter. Any suitable programming, scripting, or other type of language or combinations of languages may be used to implement the teachings contained herein in software to be used in programming or configuring a computing device.

Aspects of the methods disclosed herein may be performed in the operation of such computing devices. The order of the blocks presented in the examples above can be varied—for example, blocks can be re-ordered, combined, or broken into sub-blocks. Certain blocks or processes can be performed in parallel.

The foregoing description of the examples, including illustrated examples, of the subject matter has been presented only for the purpose of illustration and description and is not intended to be exhaustive or to limit the subject matter to the precise forms disclosed. Numerous modifications, adaptations, and uses thereof will be apparent to those skilled in the art without departing from the scope of this subject matter. The illustrative examples described above are given to introduce the reader to the general subject matter discussed here and are not intended to limit the scope of the disclosed concepts.

The invention claimed is:

1. A system comprising:
an implantable medical device including a programming interface to receive programming instructions in vivo in a subject to control operations of the implantable medical device;
an interface switch coupled to the programming interface to enable or disable the programming interface; and
a security interface coupled to the interface switch in vivo to prevent access to the programming interface except in response to receiving a plurality of coded activation signals produced ex vivo in proximity to different places on the subject to allow the programming interface to receive the programming instructions.

2. The system of claim 1 wherein at least one coded activation signal of the plurality of coded activation signals comprises an ultrasonic or audible acoustic signal including a coded tone.

3. The system of claim 1 wherein at least one coded activation signal of the plurality of coded activation signals comprises a magnetic field that includes at least one of a pulse frequency or predetermined pattern.

4. The system of claim 1 wherein at least one coded activation signal of the plurality of coded activation signals comprises an optical signal that includes wavelengths of light that are transmitted easily through skin and an on-off coding scheme.

5. The system of claim 1 further comprising a proximity-based security mechanism to generate at least one coded activation signal of the plurality of coded activation signals in close proximity to the subject.

6. The system of claim 5 further comprising:
a first transducer communicatively coupled to the interface switch to receive the programming instructions; and
a second transducer communicatively coupled to the security interface to receive the at least one coded activation signal from the proximity-based security mechanism.

7. A method comprising:
detecting, at or near a medical device implanted in a subject, a plurality of coded activation signals produced in close proximity to different places on the subject;
activating a programming interface for the medical device in response to the plurality of coded activation signals; and
receiving programming instructions over the programming interface while the programming interface is activated.

8. The method of claim 7 wherein at least one coded activation signal of the plurality of coded activation signals comprises a pulsed magnetic field.

9. The method of claim 8 wherein the pulsed magnetic field comprises at least one of a pulse frequency or predetermined pattern that is specifically assigned to the medical device.

10. The method of claim 7 wherein at least one coded activation signal of the plurality of coded activation signals comprises an optical signal that includes wavelengths of light that are transmitted easily through skin and an on-off coding scheme.

11. The method of claim 7 wherein at least one coded activation signal of the plurality of coded activation signals comprises an ultrasonic or audible acoustic signal including a coded tone.

12. The method of claim 7 wherein at least one coded activation signal of the plurality of coded activation signals comprises at least one of a carrier frequency or a pulse frequency specifically assigned to the medical device.

13. A non-transitory computer-readable medium that includes instructions that are executable by a computing device for causing the computing device to perform operations for activating a programming interface of a medical device implanted in a subject, the operations comprising:

receiving input from a user directed to authenticating access to the programming interface of the medical device; and transmitting a plurality of authentication signals at different places on the subject, the plurality of authentication signals comprising at least one of an acoustic signal or an optical signal configured to activate the programing interface to authenticate the access by the computing device.

14. The non-transitory computer-readable medium of claim 13 wherein the operations further comprise:

accessing an identifier for the medical device; and coding at least one of the plurality of authentication signals in accordance with the identifier for the medical device.

15. The non-transitory computer-readable medium of claim 14 wherein the at least one of the plurality of authentication signals comprises pulse coding.

16. The non-transitory computer-readable medium of claim 14 wherein the at least one of the plurality of authentication signals comprises frequency coding.

17. The non-transitory computer-readable medium of claim 13 wherein at least one of the plurality of authentication signals comprises an acoustic signal and an optical signal.

18. The non-transitory computer-readable medium of claim 13 wherein the operations further comprise sending programming instructions to the programming interface of the medical device.

* * * * *